US010898456B2

(12) United States Patent
Nogusa et al.

(10) Patent No.: US 10,898,456 B2
(45) Date of Patent: Jan. 26, 2021

(54) AMELIORATING AGENT FOR EXERCISE-INDUCED GASTROINTESTINAL DISORDERS

(71) Applicant: AJINOMOTO CO., INC., Tokyo (JP)

(72) Inventors: Yoshihito Nogusa, Kawasaki (JP); Ami Mizugaki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/835,564

(22) Filed: Dec. 8, 2017

(65) Prior Publication Data

US 2018/0098954 A1 Apr. 12, 2018

Related U.S. Application Data

(63) Continuation of application No. PCT/JP2016/067005, filed on Jun. 8, 2016.

(30) Foreign Application Priority Data

Jun. 10, 2015 (JP) ................. 2015-117758

(51) Int. Cl.
*A61K 31/198* (2006.01)
*A61K 31/4172* (2006.01)
*A23L 33/175* (2016.01)
*A61P 1/14* (2006.01)

(52) U.S. Cl.
CPC .......... *A61K 31/198* (2013.01); *A23L 33/175* (2016.08); *A61K 31/4172* (2013.01); *A61P 1/14* (2018.01)

(58) Field of Classification Search
CPC .............. A61K 31/198; A61K 31/4172; A61K 9/0053; A23L 33/175; A23L 33/30; A23V 2002/00; A61P 1/14; A61P 21/06; A61P 43/00
See application file for complete search history.

(56) References Cited

U.S. PATENT DOCUMENTS

| | | | | |
|---|---|---|---|---|
| 4,279,917 A | * | 7/1981 | Takami | A61K 38/01 514/400 |
| 5,719,133 A | * | 2/1998 | Schmidl | A23L 33/40 514/168 |
| 8,067,471 B2 | * | 11/2011 | Whippie | A61K 31/195 514/561 |
| 8,361,511 B2 | * | 1/2013 | Hill | A23D 9/00 424/498 |
| 9,066,537 B2 | * | 6/2015 | Hofman | A23L 33/185 |
| 2004/0096478 A1 | | 5/2004 | Whippie et al. | |
| 2004/0097404 A1 | | 5/2004 | Kessler et al. | |
| 2006/0068039 A1 | * | 3/2006 | Agger | A61K 31/195 424/738 |
| 2006/0247312 A1 | | 11/2006 | Whippie et al. | |
| 2007/0270355 A1 | * | 11/2007 | Garcia | A23L 33/175 514/23 |
| 2011/0183040 A1 | * | 7/2011 | Ermolin | A23L 33/40 426/72 |
| 2012/0035234 A1 | | 2/2012 | Whippie et al. | |
| 2012/0283185 A1 | | 11/2012 | Whyte | |
| 2015/0282506 A1 | * | 10/2015 | Taylor | A23K 20/121 426/2 |
| 2019/0070139 A1 | * | 3/2019 | Nogusa | A61K 31/198 |

FOREIGN PATENT DOCUMENTS

| | | |
|---|---|---|
| JP | 2002-513544 A | 5/2002 |
| JP | 2003-530411 A | 10/2003 |
| JP | 2004-513912 A | 5/2004 |
| WO | WO 99/56758 A1 | 11/1999 |
| WO | WO 01/78532 A1 | 10/2001 |
| WO | WO 2015/167002 A1 | 11/2015 |

OTHER PUBLICATIONS

Cani et al., "Changes in gut microbiota control inflammation in obese mice through a mechanism involving GLP-2-driven improvement of gut permeability", 2009, Gut, 58(8), pp. 1091-1103. (Year: 2009).*

National Center for Biotechnology Information. PubChem Database. Cystine, CID=595, https://pubchem.ncbi.nlm.nih.gov/compound/Cystine (accessed on Feb. 3, 2020; create: Sep. 16, 2004) (Year: 2004).*

National Center for Biotechnology Information. PubChem Database. Cysteine, CID=5862, https://pubchem.ncbi.nlm.nih.gov/compound/Cysteine (accessed on Feb. 3, 2020; create: Sep. 16, 2004) (Year: 2004).*

English translation of the International Search Report and Written Opinion of the International Searching Authority dated Sep. 6, 2016 in PCT/JP2016/067005, 9 pages.

Shigekazu Kurihara, et al., "Cystine and Theanine: Amino Acids as Oral Immunomodulative Nutrients" SpringerPlus, 2013, vol. 2, No. 635, pp. 1-7.

(Continued)

*Primary Examiner* — My-Chau T. Tran
(74) *Attorney, Agent, or Firm* — Oblon, McClelland, Maier & Neustadt, L.L.P.

(57) ABSTRACT

Ingesting an agent containing cystine or a salt thereof, as an active ingredient, is effective for improving exercise-induced gastrointestinal disorder, providing an improvement effect equal to or better than that by the conventional technology on exercise-induced gastrointestinal disorders including exercise-induced decline in gastrointestinal tract barrier function.

12 Claims, 5 Drawing Sheets

(56) References Cited

OTHER PUBLICATIONS

Shizuo Sakamoto, "Over Training Shokogun to sono Taishoho ni Tsuite Oshiete Kudasai" The Journal of Therapy, vol. 88, No. 6, 2006, pp. 1797-1799.

Micah Zuhl, et al., "Exercise Regulation of Intestinal Tight Junction Proteins" Br. J. Sports Med., vol. 48, 2014, pp. 980-986 and cover pages.

Micah N. Zuhl, et al., "Effects of Oral Glutamine Supplementation on Exercise-Induced Gastrointestinal Permeability and Tight Junction Protein Expression" J. Appl. Physiol., vol. 116, 2014, pp. 183-191.

Kátie Anunciação Costa, et al., "L-Arginine Supplementation Prevents Increases in Intestinal Permeability and Bacterial Translocation in Male Swiss Mice Subjected to Physical Exercise under Environmental Heat Stress" The Journal of Nutrition, vol. 144, 2014, pp. 218-223.

Marleen TJ Van Ampting, et al., "Intestinal Barrier Function in Response to Abundant or Depleted Mucosal Glutathione in *Salmonella*-Infected Rats" BMC Physiology, vol. 9, No. 6, 2009, pp. 1-9.

Kim Van Wijck, et al. "Exercise-Induced Splanchnic Hypoperfusion Results in Gut Dysfunction in Healthy Men" PLoS ONE, vol. 6, Issue 7, Jul. 2011, pp. e 22366 1-9.

Tetsuro Shibakusa, et al. "Enhancement of Postoperative Recovery by Preoperative Oral Co-Administration of the Amino Acids, Cystine and Theanine, in a Mouse Surgical Model" Clinical Nutrition, vol. 31, 2012, pp. 555-561.

Shigeki Murakami, et al., "Suppression of Exercise-Induced Neutrophilia and Lymphopenia in Athletes by Cystine/Theanine Intake: a Randomized, Double-Blind, Placebo-Controlled Trial" Journal of the International Society of Sports Nutrition, vol. 7, 2010, pp. 1-11.

Shigeki Murakami, et al. "Effects of Oral Supplementation with Cystine and Theanine on the Immune function of Athletes in Endurance Exercise: Randomized, Double-Blind, Placebo-Controlled Trial" Biosci. Biotechnol. Biochem., vol. 73, Issue 4, 2009, pp. 817-821.

\* cited by examiner

AMELIORATING AGENT FOR EXERCISE-INDUCED GASTROINTESTINAL DISORDERS

CROSS REFERENCES TO RELATED APPLICATIONS

This application is a continuation of International Patent Application No. PCT/JP2016/067005, filed on Jun. 8, 2016, and claims priority to Japanese Patent Application No. 2015-117758, filed on Jun. 10, 2015, both of which are incorporated herein by reference in their entireties.

BACKGROUND OF THE INVENTION

Field of the Invention

The present invention relates to agents and methods for improving an exercise-induced gastrointestinal disorder.

Discussion of the Background

The gastrointestinal tract simultaneously not only provides digestive absorption of ingested food but also a barrier function to prevent foreign substances from entering the body. It is known that the decline in the barrier function leads to intrusion of enteric bacteria into the body, inducing inflammation to cause general physical deterioration as well as upset of the gastrointestinal tract. In severe cases, bacteria may migrate to organs, resulting in multiple organ failure. Such decline in the barrier function of the gastrointestinal tract is caused by intense exercise (see Wijck et al. (2011) Plos One 6 (7) e22366, which is incorporated herein by reference inits entirety). Although decline in the gastrointestinal tract function due to exercise is partly similar to Crohn's disease, ulcerative colitis and stress disorders, there are many unknown aspects in the detailed mechanism. Currently, it is considered that the barrier function decreases due to physiological phenomena peculiar to exercise, such as blood collected by the muscle and heart during exercise, reduced blood supply to the gastrointestinal tract, body temperature rise and the like. Since decline in the barrier function leads to a decrease in athletes' condition and performance, maintenance of the barrier function of the gastrointestinal tract is important for an athlete.

As those that improve exercise-induced decline in gastrointestinal tract barrier function, cow colostrum, glutamine, and arginine have been reported. In cow colostrum, it has been reported that the stress resistance of the intestine is increased by growth factors such as TGF-1 and the like contained therein (see National Publication of International Patent Application No. 2002-513544, which, is incorporated herein by reference in its entirety). However, cow colostrum is valuable and has a problem of lack of broad utility.

Zuhl et al. (2014) J. Appl. Physiol. 116, 183-191, and Costa et al. (2014) J Nutr. 144, 218-223, both of which are incorporated herein by reference in their entireties, have reported that ingestion of glutamine or arginine for one week alleviates exercise-induced decline in gastrointestinal tract barrier function.

However, improvement effects of glutamine and arginine on exercise-induced decline in gastrointestinal tract barrier function are not sufficient. Furthermore, glutamine has a problem of low stability in aqueous solution, which limits application thereof.

National Publication of International Patent Application No. 2004-513912, which is incorporated herein by reference in its entirety, reports a supplement to be intestinally administered to maintain or restore the intestinal barrier of the intestines of patients with critical condition or chronic disease and malnourished people.

However, National Publication of International Patent Application No. 2004-513912 provides no description relating to exercise-induced gastrointestinal disorders, and does not describe actual use of cystine. In addition, the supplement described in patent document 2: National Publication of International Patent Application No. 2004-513912 is administered intestinally, and is not ingested orally.

Shibakusa et al. (2012) Clin. Nutr. 31, 555-561, which is incorporated herein by reference in its entirety, reports that oral administration of cystine and theanine before surgery suppresses gastrointestinal inflammation in a mouse surgery (small intestine manipulation) model.

However, the model used in Shibakusa et al. (2012) Clin. Nutr. 31, 555-561, is not a model that developed inflammation of the gastrointestinal tract by exercise, but a model that developed inflammation of the gastrointestinal tract by physical injury (small intestine manipulation). In addition, data evaluating gastrointestinal permeability is not described.

Murakami et al. (2010) J. Int. Soc. Sports. Nutr. 7:23, which is incorporated herein by reference inits entirety, reports that, by letting long-distance runners ingest cystine and theanine, immune depression during exercise was suppressed and muscle disorder after exercise was relieved.

However, improvement of immune depression during exercise is not related to the improvement of exercise-induced gastrointestinal disorder. In addition, Murakami et al. (2010) J. Int. Soc. Sports. Nutr. 7:23, does not describe data evaluating gastrointestinal permeability.

Murakami et al.(2009) Biosci. Biotechnol. Biochem. 73 (4), 817-821, which is incorporated herein by reference in its entirety, reports that, by letting long-distance runners ingest cystine and theanine, immune depression during exercise was suppressed and systemic inflammation was suppressed.

However, as mentioned above, improvement of immune depression during exercise is not related to the improvement of exercise-induced gastrointestinal disorder. Even if systemic inflammation is suppressed, it does not necessarily improve decline in gastrointestinal tract barrier function. Murakami et al. (2009) Biosci. Biotechnol. Biochem. 73 (4), 817-821, does not at all study exercise-induced gastrointestinal disorders.

Thus, there remains a need for agents and methods for improving an exercise-induced gastrointestinal disorder.

SUMMARY OF THE INVENTION

Accordingly, it is one object of the present invention to provide novel agents for improving exercise-induced gastrointestinal disorder.

It is another object of the present invention to provide novel agents for improving exercise-induced gastrointestinal disorder, which are capable of providing an improvement effect equal to or better than that by the conventional technology on exercise-induced gastrointestinal disorders including exercise-induced decline in gastrointestinal tract barrier function.

It is another object of the present invention to provide novel methods for improving exercise-induced gastrointestinal disorder.

These and other objects, which will become apparent during the following detailed description, have been achieved by the inventors' discovery that cystine is superior in an improving effect for exercise-induced gastrointestinal disorders (e.g., decline in gastrointestinal tract barrier function and gastrointestinal upset etc.), and conducted further studies based on the finding.

Accordingly, the present invention provides:

(1) An agent for improving an exercise-induced gastrointestinal disorder, comprising cystine or a salt thereof as an active ingredient.

(2) The agent of (1), wherein the gastrointestinal disorder is at least one selected from decline in gastrointestinal tract barrier function and gastrointestinal upset.

(3) The agent of (1) or (2), wherein a content of cystine or a salt thereof is not less than 0.1 wt % relative to the all amino acids contained therein.

(4) The agent of any one of (1) to (3), wherein a content 5 of cystine or a salt thereof is 6 mg to 12 g per one intake by human.

(5) The agent of any one of (1) to (4), composed of a unit package form per intake and comprising 6 mg to 12 g of cystine or a salt thereof as one intake in the unit. (6) The agent of any one of (1) to (5), further comprising at least one selected from the group consisting of glutamine, serine, histidine, arginine, valine, leucine, isoleucine and a salt thereof.

(7) The agent of (6), wherein a total of a content of cystine or a salt thereof and a content of at least one selected from the group consisting of glutamine, serine, histidine, arginine, valine, leucine, isoleucine and a salt thereof is not less than 10 wt % relative to all amino acids contained therein. (8) The agent of (6) or (7), wherein a weight ratio of (a) a content of cystine or a salt thereof, and (b) a content of at least one selected from the group consisting of glutamine, serine, histidine, arginine, valine, leucine, isoleucine and a salt thereof is (a):(b)=1:0.01 to 10.

(9) The agent of any one of (1) to (8), that is orally ingested.

(10) The agent of any one of (1) to (9), that is ingested at least one time before start of exercise.

(11) The agent of any one of (1) to (10), that is ingested during exercise or after completion of the exercise.

(12) The agent of any one of (1) to (11), wherein a content of cystine or a salt thereof is the highest or second highest in all amino acids contained therein.

(13) The agent of any one of (1) to (12), that is a prophylaxis or therapeutic agent for exercise-induced gastrointestinal disorder.

(14) A food or medicament comprising the agent of any one of (1) to (13).

(15) A commercial package comprising the agent of any one of (1) to (13) and a written matter associated therewith, the written matter stating that the agent can or should be used for improving an exercise-induced gastrointestinal disorder.

(16) A method of improving an exercise-induced gastrointestinal disorder, comprising ingestion of an effective amount of an agent containing cystine or a salt thereof as an active ingredient at least one time by a subject in need thereof.

(17) The method of (16), wherein the gastrointestinal disorder is at least one selected from decline in gastrointestinal tract barrier function and gastrointestinal upset.

(18) The method of (16) or (17), wherein a content of cystine or a salt thereof in the aforementioned agent is not less than 0.1 wt % relative to all amino acids contained in the aforementioned agent.

(19) The method of any one of (16) to (18), wherein a content of cystine or a salt thereof in the aforementioned agent is 6 mg to 12 g per one intake by human.

(20) The method of any one of (16) to (19), wherein the aforementioned agent is composed of a unit package form per intake and comprises 6 mg to 12 g of cystine or a salt thereof as one intake in the unit.

(21) The method of any one of (16) to (20), wherein the aforementioned agent further comprising at least one selected from the group consisting of glutamine, serine, histidine, arginine, valine, leucine, isoleucine and a salt thereof.

(22) The method of (21), wherein a total of a content of cystine or a salt thereof and a content of at least one selected from the group consisting of glutamine, serine, histidine, arginine, valine, leucine, isoleucine and a salt thereof in the aforementioned agent is not less than 10 wt % relative to all amino acids contained in the aforementioned agent.

(23) The method of (21) or (22), wherein a weight ratio of (a) a content of cystine or a salt thereof in the aforementioned agent, and (b) a content of at least one selected from the group consisting of glutamine, serine, histidine, arginine, valine, leucine, isoleucine and a salt thereof in the aforementioned agent is (a):(b)=1:0.01 to 10.

(24) The method of any one of (16) to (23), wherein the aforementioned agent is orally ingested.

(25) The method of any one of (16) to (24), wherein the aforementioned agent is ingested at least one time before start of exercise.

(26) The method of any one of (16) to (25), wherein the aforementioned agent is ingested during exercise or after completion of the exercise.

(27) The method of any one of (16) to (26), wherein a content of cystine or a salt thereof in the aforementioned agent is the highest or second highest in all amino acids contained therein.

(28) The method of any one of (16) to (27), that is a prophylaxis or therapeutic method for exercise-induced gastrointestinal disorder.

(29) A method of improving an exercise-induced gastrointestinal disorder, comprising ingestion of an effective amount of an agent containing cystine or a salt thereof as an active ingredient at least one time by a subject in need thereof (excluding medical practice).

(30) The agent of any one of (1) to (13), that is a food composition.

(31) A food composition for improving an exercise-induced gastrointestinal disorder, comprising cystine or a salt thereof as an active ingredient.

(32) The food composition of (31), wherein the gastrointestinal disorder is at least one selected from decline in gastrointestinal tract barrier function and gastrointestinal upset.

(33) The food composition of (31) or (32), wherein a content of cystine or a salt thereof is not less than 0.1 wt % relative to all amino acids contained therein.

(34) The food composition of any one of (31) to (33), wherein a content of cystine or a salt thereof is 6 mg to 12 g per one intake by human.

(35) The food composition of any one of (31) to (34), that is composed of a unit package form per intake and comprising 6 mg-12 g of cystine or a salt thereof as one intake in the unit.

(36) The food composition of any one of (31) to (35), further comprising at least one selected from the group consisting of glutamine, serine, histidine, arginine, valine, leucine, isoleucine and a salt thereof.

(37) The food composition of (36), wherein a total of a content of cystine and a content of at least one selected from the group consisting of glutamine, serine, histidine, arginine, valine, leucine, isoleucine and a salt thereof is not less than 10 wt % relative to all amino acids contained therein.

(38) The food composition of (36) or (37), wherein a weight ratio of (a) a content of cystine, and (b) a content of at least one selected from the group consisting of glutamine, serine, histidine, arginine, valine, leucine, isoleucine and a salt thereof is (a):(b)=1:0.01 to 10.

(39) The food composition of any one of (31) to (38), that is ingested at least one time before start of exercise.

(40) The food composition of any one of (31) to (39), that is ingested during exercise or after completion of the exercise.

(41) The food composition of any one of (31) to (40), wherein a content of cystine or a salt thereof is the highest or second highest in all amino acids contained therein.

Effect of the Invention

The agent of the present invention is preferably used for improving an exercise-induced gastrointestinal disorder. Particularly, the agent of the present invention is effectively used for improving exercise-induced decline in gastrointestinal tract barrier function (preferably, decline in barrier function of small intestine and/or large intestine) and/or exercise-induced gastrointestinal upset.

In addition, since the agent of the present invention contains amino acid with rich eating experiences such as cystine and the like as an active ingredient, it is extremely advantageous since it has high safety and scarce side effects.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

In the present invention, the "exercise-induced gastrointestinal disorder" refers to a gastrointestinal disorder expressed along with exercise (particularly, intense exercise). The "intense exercise" here means exercise for a long time, daily exercise, relatively high intensity exercise, exercise in a harsh environment such as high temperature and the like, or the like. The "gastrointestinal disorder" refers to tissue damage and functional decline in the gastrointestinal tract (pharynx, esophagus, stomach, small intestine (duodenum, jejunum, ileum), large intestine) and symptoms expressed due to them. Examples thereof include decline in gastrointestinal tract barrier function and gastrointestinal upset and the like.

As a method for determining whether or not the gastrointestinal disorder is exercise-induced, when, for example, a gastrointestinal disorder occurs though significant rise in TNF-α cannot be confirmed, the gastrointestinal disorder can be judged to be exercise-induced. Whether or not a gastrointestinal disorder is exercise-induced can also be judged not only from TNF-α but, for example, increase in body temperature, blood shortage, development of inflammation (particularly, inflammation with unremarkable increase in TNF-α) or the like.

The transport pathway of a substance via a gastrointestinal epithelial cell is largely divided into a transcellular pathway and a paracellular pathway. The transcellular pathway contributes to the absorption of nutrients via transporters and channels on the cellular membrane. On the other hand, in the paracellular pathway, selective permeability is controlled by adhesion molecules between adjacent cells, and the pathway is useful for the absorption of minerals such as calcium and the like, as well as shows a barrier function to prevent enteric bacteria present in large amounts in the lumen and antigens derived from foods from invading the body. An adhesion molecular structure in charge of the selective permeability is a tight junction. The tight junction is a huge protein complex localized near the brush border membrane of epithelial cell basolateral membrane, and is composed of transmembrane proteins such as occludin, claudin and the like and intracellular scaffold proteins such as zonula occludens and the like.

Figure 1:
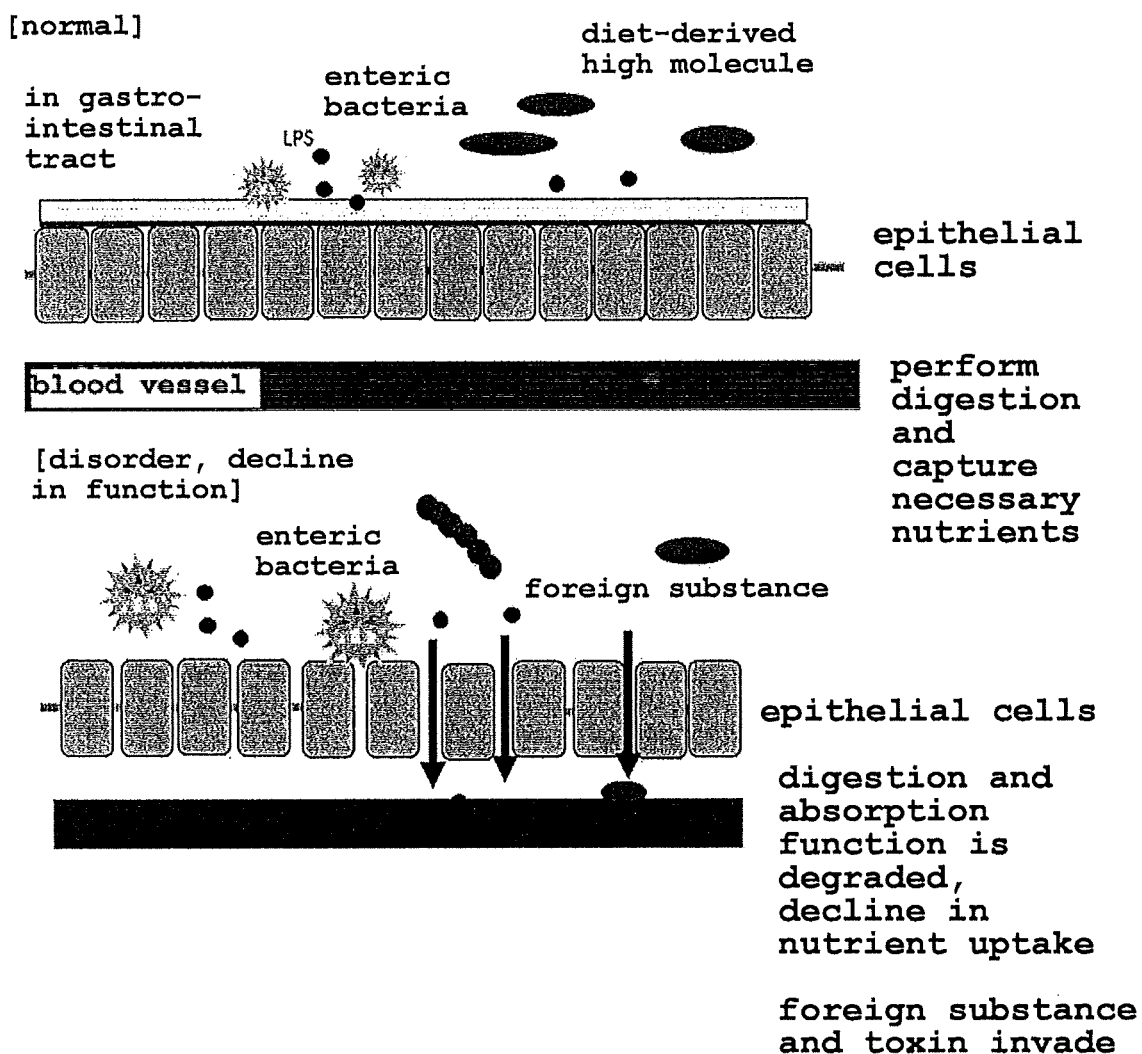
FIG. 1 is a schematic figure showing decline in the gastrointestinal tract barrier function. LPS: lipopolysaccharide.

In the present invention, the "exercise-induced decline in gastrointestinal tract barrier function" refers to the collapse of barrier between epithelial cells of the gastrointestinal tract (pharynx, esophagus, stomach, small intestine (duodenum, jejunum, ileum), large intestine) associated with exercise (particularly, intense exercise), and refers to a state in which permeability of the gastrointestinal tract is enhanced and foreign substances, enteric bacteria, toxins produced by enteric bacteria or the like easily enter the body through the gastrointestinal tract. Decline in the gastrointestinal tract barrier function is considered to be caused, for example, by a decrease in the blood supply to the gastrointestinal tract during exercise. Also, decline in the gastrointestinal tract barrier function is considered to be caused, for example, by an increase in body temperature and the like. A schematic figure of the decline in the gastrointestinal tract barrier function is shown in FIG. 1. The main cause of the "exercise-induced decline in the gastrointestinal tract barrier function" is considered to be an increase in body temperature or blood flow decline due to exercise. On the other hand, stress bowel disease and inflammatory bowel disease are caused by inflammation, and these and the exercise-induced decline in gastrointestinal tract barrier function are considered to be different in the mechanism and condition.

Decline in the gastrointestinal tract barrier function and the presence or absence of improvement thereof can be confirmed by orally administering a labeled compound having a molecular weight whose transfer from the gastrointestinal tract to the body is suppressed when the barrier function of the gastrointestinal tract is maintained normal, and whose permeation through the gastrointestinal tract and transfer to the blood occurs when the barrier function of the gastrointestinal tract decreased (e.g., molecular weight about 4000) to an animal and measuring the amount (concentration) of the labeled compound in the blood. In the case of human, they can be confirmed by measuring the intestinal mucosa permeation amount of non-metabolizable sugar molecules such as mannitol, rhamnose, lactulos and the like.

In the present invention, the "exercise-induced gastrointestinal upset" refers to gastrointestinal upset expressed along with exercise (particularly, intense exercise). As used herein, the "gastrointestinal upset" is a generic term for pathological symptom developed in the gastrointestine, and pathological symptoms developed due to decline in the gastrointestinal function and, for example, appetite decline, stomach pain, vomiting, diarrhea and the like can be mentioned.

In the present invention, "improvement" of the exercise-induced gastrointestinal disorder means, for example, significant suppression of exercise-induced decline in gastrointestinal barrier function during exercise, significant suppression of stomach pain, vomiting and decline in digestive capacity during or after exercise, which are induced by exercise, significant suppression of decreased appetite after exercise, and prevention of intrusion of enteric bacteria and toxins derived from bacteria into the body and alleviation of deterioration of physical condition.

In the present invention, moreover, "improvement" includes "prophylaxis or treatment". The "prophylaxis" of exercise-induced gastrointestinal disorder means prevention or delay of the onset of an exercise-induced gastrointestinal disorder, and "treatment" means alleviation of the symptoms of exercise-induced gastrointestinal disorder, or prevention or delay of the progress (exacerbation) of the symptoms.

As cystine contained as an active ingredient in the agent of the present invention, any of L-form, D-form and DL-form can be used. It is preferably L-form or DL-form, further preferably L-form.

As cystine, not only a free form but also a salt form can be used. The term "cystine" in the present invention is a concept encompassing even a salt. Examples of the salt form include acid addition salt, salt with a base and the like, and a pharmacologically acceptable salt is preferably selected.

Concrete examples of the cystine salt include salts with inorganic bases, salts with inorganic acids, salts with organic acids and the like. Examples of the salts with inorganic bases include salts with alkali metals such as sodium, potassium, lithium and the like, salts with alkaline earth metals such as calcium, magnesium and the like, ammonium salt and the like. Examples of the salts with inorganic acids include salts with hydrohalic acid (hydrochloric acid, hydrobromic acid, hydroiodic acid, etc.), sulfuric acid, nitric acid, phosphoric acid and the like. Examples of the salts with organic acids include salts with formic acid, acetic acid, propionic acid, oxalic acid, succinic acid, maleic acid, fumaric acid, citric acid and the like.

In the present invention, the cystine to be used may be extracted from animals, plants or the like, which are naturally present, and purified, or obtained by a chemical synthesis method, a fermentation method, an enzyme method or a gene recombinant method.

The content of cystine in the agent of the present invention is preferably not less than 2.5 mg, more preferably not less than 6 mg, further preferably not less than 10 mg, particularly preferably not less than 70 mg, per one intake by human, from the aspect of an improvement effect on gastrointestinal disorders. From the aspect of easy ingestion, the above-mentioned content is preferably not more than 15 g, more preferably not more than 12 g, further preferably not more than 10 g, per one intake by human. In the present invention, the content of amino acid such as cystine and the like is calculated after converting the salt to a free form when the amino acid forms a salt.

In the present invention, "one intake" is an amount ingested or administered at one time.

From the aspect of improvement effect on gastrointestinal disorders, the content of cystine is preferably not less than 0.1 wt %, more preferably not less than 1 wt %, more preferably not less than 3 wt %, particularly preferably not less than 10 wt %, relative to all amino acids contained in the agent of the present invention. From the aspect of improvement effect on gastrointestinal disorders, moreover, the content of cystine is preferably not more than 100 wt %, more preferably not more than 90 wt %, particularly preferably not more than 80 wt %, relative to all amino acids contained in the agent of the present invention.

The content of cystine is preferably the highest or second highest in all amino acids contained in the agent of the present invention. When the content of cystine is the highest or second highest in all amino acids contained in the agent of the present invention, an efficient function as an active ingredient can be exhibited.

The agent of the present invention may further contain, in addition to cystine, at least one selected from the group consisting of glutamine, serine, histidine, arginine, valine, leucine and isoleucine. The agent of the present invention further containing, in addition to cystine, at least one selected from the group consisting of glutamine, serine, histidine, arginine, valine, leucine and isoleucine can enhance an improvement effect on exercise-induced gastrointestinal disorders. Of these, since glutamine is easily utilized as an energy source of gastrointestinal cells, the agent of the present invention preferably further contains glutamine in addition to cystine.

In the present invention, as glutamine, serine, histidine, arginine, valine, leucine and isoleucine, any of L-form, D-form and DL-form can be respectively used. They are each preferably L-form or DL-form, further preferably L-form. Not only a free form but also a salt form thereof can be used. The terms "glutamine", "serine", "histidine", "arginine", "valine", "leucine" and "isoleucine" in the present invention are each a concept encompassing even a salt. Examples of the salt form include acid addition salt, salt with a base and the like, and a pharmacologically acceptable salt is preferably selected.

Examples of the glutamine salt include salts with inorganic bases, salts with inorganic acids, salts with organic acids and the like. Examples of the salts with inorganic bases include salts with alkali metals such as sodium, potassium, lithium and the like, salts with alkaline earth metals such as calcium, magnesium and the like, ammonium salt and the like. Examples of the salts with inorganic acids include salts with hydrohalic acid (hydrochloric acid, hydrobromic acid, hydroiodic acid, etc.), sulfuric acid, nitric acid, phosphoric acid and the like. Examples of the salts with organic acids include salts with formic acid, acetic acid, propionic acid, oxalic acid, succinic acid, maleic acid, fumaric acid, citric acid and the like.

Examples of the serine salt include salts with inorganic bases, salts with inorganic acids, salts with organic acids and the like. Examples of the salts with inorganic bases include salts with alkali metals such as sodium, potassium, lithium and the like, salts with alkaline earth metals such as calcium, magnesium and the like, ammonium salt and the like. Examples of the salts with inorganic acids include salts with hydrohalic acid (hydrochloric acid, hydrobromic acid, hydroiodic acid, etc.), sulfuric acid, nitric acid, phosphoric acid and the like. Examples of the salts with organic acids include salts with formic acid, acetic acid, propionic acid, oxalic acid, succinic acid, maleic acid, fumaric acid, citric acid, glutamic acid, aspartic acid and the like.

Examples of the histidine salt include salts with inorganic bases, salts with inorganic acids, salts with organic acids and the like. Examples of the salts with inorganic bases include salts with alkali metals such as sodium, potassium, lithium and the like, salts with alkaline earth metals such as calcium, magnesium and the like, ammonium salt and the like. Examples of the salts with inorganic acids include salts with hydrohalic acid (hydrochloric acid, hydrobromic acid, hydroiodic acid, etc.), sulfuric acid, nitric acid, phosphoric acid and the like. Examples of the salts with organic acids include salts with formic acid, acetic acid, propionic acid, oxalic acid, succinic acid, maleic acid, fumaric acid, citric acid and the like.

Examples of the arginine salt include salts with inorganic bases, salts with inorganic acids, salts with organic acids and the like. Examples of the salts with inorganic bases include salts with alkali metals such as sodium, potassium, lithium and the like, salts with alkaline earth metals such as calcium, magnesium and the like, ammonium salt and the like. Examples of the salts with inorganic acids include salts with hydrohalic acid (hydrochloric acid, hydrobromic acid, hydroiodic acid, etc.), sulfuric acid, nitric acid, phosphoric acid and the like. Examples of the salts with organic acids include salts with formic acid, acetic acid, propionic acid, oxalic acid, succinic acid, maleic acid, fumaric acid, citric acid and the like.

Examples of the acids to be added to isoleucine, leucine and valine to each form a pharmacologically acceptable salt include inorganic acids such as hydrogen chloride, hydrogen bromide, sulfuric acid, phosphoric acid and the like; and organic acids such as acetic acid, lactic acid, citric acid, tartaric acid, maleic acid, fumaric acid, monomethylsulfuric acid and the like.

Examples of the pharmacologically acceptable bases of isoleucine, leucine and valine include metal hydroxides or carbonates such as sodium, potassium, calcium and the like, inorganic bases such as ammonia and the like; and organic bases such as ethylenediamine, propylenediamine, ethanolamine, monoalkyl ethanolamine, dialkyl ethanolamine, diethanolamine, triethanolamine and the like.

In the present invention, glutamine, serine, histidine, arginine, valine, leucine and isoleucine to be used may be each extracted from animals, plants or the like, which are naturally present, and purified, or obtained by a chemical synthesis method, a fermentation method, an enzyme method or a gene recombinant method.

When the agent of the present invention contains, in addition to cystine, at least one selected from the group consisting of glutamine, serine, histidine, arginine, valine, leucine and isoleucine, the content of at least one selected from the group consisting of glutamine, serine, histidine, arginine, valine, leucine and isoleucine is preferably not less than 0.1 wt %, more preferably not less than 1 wt %, particularly preferably not less than 3 wt %, relative to all amino acids contained in the agent of the present invention, from the aspects of easy administration, stability and function. In this case, the content of at least one selected from the group consisting of glutamine, serine, histidine, arginine, valine, leucine and isoleucine is preferably not more than 99 wt %, more preferably not more than 90 wt %, particularly preferably not more than 80 wt %, relative to all amino acids contained in the agent of the present invention, from the aspects of easy administration, stability and function.

In the present invention, when the agent of the present invention contains, in addition to cystine, one selected from the group consisting of glutamine, serine, histidine, arginine, valine, leucine and isoleucine, "the content of at least one selected from the group consisting of glutamine, serine, histidine, arginine, valine, leucine and isoleucine" is the content of said one component and, when the agent of the present invention contains, in addition to cystine, two or more selected from the group consisting of glutamine, serine, histidine, arginine, valine, leucine and isoleucine, it is the content of a total of the two or more components.

When the agent of the present invention contains, in addition to cystine, at least one selected from the group consisting of glutamine, serine, histidine, arginine, valine, leucine and isoleucine, the content of at least one selected from the group consisting of glutamine, serine, histidine, arginine, valine, leucine and isoleucine is preferably not less than 10 mg, more preferably not less than 50 mg, particularly preferably not less than 100 mg, per one intake by human, from the aspects of easy administration, stability and function. In this case, the content of at least one selected from the group consisting of glutamine, serine, histidine, arginine, valine, leucine and isoleucine is preferably not more than 10 g, more preferably not more than 5 g, per one intake by human, from the aspect of easy ingestion.

When the agent of the present invention contains, in addition to cystine, at least one selected from the group consisting of glutamine, serine, histidine, arginine, valine, leucine and isoleucine, a total of the cystine content and the content of at least one selected from the group consisting of glutamine, serine, histidine, arginine, valine, leucine and isoleucine is preferably not less than 0.2 wt %, more preferably not less than 2 wt %, further preferably not less than 6 wt %, particularly preferably not less than 10 wt %, relative to all amino acids contained in the agent of the present invention, from the aspect of improvement effect on exercise-induced gastrointestinal disorders. In this case, a total of the cystine content and the content of at least one selected from the group consisting of glutamine, serine, histidine, arginine, valine, leucine and isoleucine is preferably not more than 100 wt %, more preferably not more than 95 wt %, particularly preferably not more than 90 wt %, relative to all amino acids contained in the agent of the present invention, from the aspects of easy administration, stability and function. When the agent of the present invention contains, in addition to cystine, at least one selected from the group consisting of glutamine, serine, histidine, arginine, valine, leucine and isoleucine, a weight ratio of (a) a content of cystine, and (b) a content of at least one selected from the group consisting of glutamine, serine, histidine, arginine, valine, leucine and isoleucine is preferably (a):(b) =1:0.01 to 100, more preferably 1:0.01 to 50, further preferably 1:0.01 to 25, still more preferably 1:0.01 to 10, particularly preferably 1:0.02 to 10, most preferably 1:0.1 to 10, from the aspect of the function of each amino acid.

When the agent of the present invention contains, in addition to cystine, isoleucine, leucine and valine, a weight ratio of respective contents of isoleucine, leucine and valine is generally isoleucine:leucine:valine=1:1.5 to 2.5:0.8 to 1.7, particularly preferably 1:1.9 to 2.2:1.1 to 1.3.

It is preferable that the agent of the present invention does not substantially contain non-proteinogenic amino acid other than cystine. When the agent of the present invention does not substantially contain non-proteinogenic amino acid other than cystine, it is possible to achieve functionality of sufficiently supplying the protein starting material necessary for exercise and improving exercise-induced gastrointestinal disorder even when the dose is limited.

Examples of non-proteinogenic amino acid other than cystine include theanine, ornithine, citrulline, taurine, GABA (γ-amino butyric acid) and the like. Of these, since theanine cannot directly be a protein starting material, the agent of the present invention preferably does not substantially contain theanine.

In the present invention, non-proteinogenic amino acid other than cystine (e.g., theanine etc.) is "not substantially contained" means (1) non-proteinogenic amino acid other than cystine is not contained at all, or (2) non-proteinogenic amino acid other than cystine is contained to an extent that does not affect the effect of the present invention (specifically, generally not more than 28 wt %, preferably not more than 20 wt %, more preferably not more than 10 wt %, further preferably not more than 1 wt %, particularly preferably not more than 0.1 wt %, relative to all amino acids contained in the agent of the present invention).

The agent of the present invention can also be used in combination with a therapeutic drug for gastrointestinal ulcer (hereinafter sometimes to be referred to as a concomitant drug). The concomitant drug is not particularly limited as long as it is a therapeutic drug generally used for the treatment of digestive system diseases, and specifically, rebamipide and the like can be mentioned.

The agent of the present invention can also be used in combination with good bacteria such as lactic acid bacterium and bifidobacteria1. Good bacteria are not particularly limited, and specifically, VSL #3 (registered trade mark) and the like can be mentioned.

As the application target of the agent of the present invention, mammals (e.g., human, mouse, rat, hamster, rabbit, cat, dog, bovine, sheep, monkey etc.) can be mentioned. When the agent of the present invention is applied to mammals other than human, the ingestion amount of the agent of the present invention can be appropriately set according to the body weight, size and the like of the mammal.

While the agent of the present invention is generally ingested orally, administration routes such as enteral tube administration, administration by infusion and the like can be employed according to the symptom of the application target. Examples of the dosage form when the agent of the present invention is orally ingested include granule, fine granule, powder, coating tablet, tablet, powder, (micro) capsule, chewable, syrup, juice, liquid, suspension, emulsion and the like.

These dosage forms can be prepared by a conventional method. When necessary for formulation, various pharmacologically acceptable substances for formulation can be added. While the substances for formulation can be appropriately selected according to the dosage form of the agent of the present invention, for example, excipient, diluent, additive, disintegrant, binder, coating agent, lubricant, glidant, lubricant, corrigent, flavoring agent, sweetening agent, solubilizer and the like can be mentioned. Specific examples of the substances for formulation include magnesium carbonate, titanium dioxide, saccharides (e.g., lactose, mannitol etc.), talc, milk protein, gelatin, starch, cellulose and a derivative thereof, animal and vegetable oil, polyethylene glycol, solvent (e.g., sterile water etc.), monovalent or polyvalent alcohol (e.g., glycerol etc.) and the like.

While the ingestion amount of the agent of the present invention varies depending on the symptom, age, body weight of the application target, dosage form, ingestion method, administration method and the like, when the application target is an adult, the agent of the present invention can be used for the ingestion of generally 0.1 mg/kg body weight to 2 g/kg body weight, preferably 1 mg/kg body weight to 1 g/kg body weight, more preferably 5 mg/kg body weight to 0.2 g/kg body weight, of cystine per day.

When the agent of the present invention contains, in addition to cystine, at least one selected from the group consisting of glutamine, serine, histidine, arginine, valine, leucine and isoleucine, and the application target is an adult, the agent of the present invention can be used for the ingestion of at least one selected from the group consisting of glutamine, serine, histidine, arginine, valine, leucine and isoleucine in the following amount.

glutamine: generally 0.1 mg/kg body weight to 5 g/kg body weight, preferably 1 mg/kg body weight to 4 g/kg body weight, more preferably 5 mg/kg body weight to 2 g/kg body weight, per day serine: generally 0.1 mg/kg body weight to 4 g/kg body weight, preferably 1 mg/kg body weight to 2 g/kg body weight, more preferably 5 mg/kg body weight to 1 g/kg body weight, per day histidine: generally 0.1 mg/kg body weight to 4 g/kg body weight, preferably 1 mg/kg body weight to 2 g/kg body weight, more preferably 5 mg/kg body weight to 1 g/kg body weight, per day arginine: generally 1 mg/kg body weight to 4 g/kg body weight, preferably 1 mg/kg body weight to 2 g/kg body weight, more preferably 0.02 g/kg body weight to 1 g/kg body weight, per day valine: generally 0.1 mg/kg body weight to 4 g/kg body weight, preferably 1 mg/kg body weight to 2 g/kg body weight, more preferably 5 mg/kg body weight to 1 g/kg body weight, per day leucine: generally 0.1 mg/kg body weight to 4 g/kg body weight, preferably 1 mg/kg body weight to 2 g/kg body weight, more preferably 5 mg/kg body weight to 1 g/kg body weight, per day isoleucine: generally 1 mg/kg body weight to 4 g/kg body weight, preferably 1 mg/kg body weight to 2 g/kg body weight, more preferably 5 mg/kg body weight to 1 g/kg body weight, per day The above-mentioned ingestion amount can be taken once or in two or more portions (e.g., 2 to 5 portions) per day.

When the application target is an adult, the agent of the present invention can be used such that the total ingestion amount of all amino acids would be generally 0.1 mg/kg body weight to 4 g/kg body weight, per day. Particularly, when the application target is, for example, an athlete or the like, the agent of the present invention can be used such that the total ingestion amount of all amino acids would be preferably 0.01 g/kg body weight to 2 g/kg body weight, more preferably 0.05 g/kg body weight to 1 g/kg body weight, per day, from the aspects of the function of the agent of the present invention and the protein amount to be ingested by an athlete per day.

The timing of ingestion of the agent of the present invention is not particularly limited, and may be, for example, before start of exercise, during exercise, after completion of the exercise or the like. From the viewpoint that the agent of the present invention is favorably exposed to the gastrointestinal tract before starting the exercise, it is preferably before start of exercise.

While the number of ingestion of the agent of the present invention is not particularly limited, it is at least once (once or twice or more). From the viewpoint of convenience of utilization and functionality, the agent of the present invention is preferably ingested at least once before starting exercise. Also, the agent of the present invention may be ingested at least once before starting exercise, and further at least once during exercise and/or after completion of the exercise.

When the number of ingestion of the agent of the present invention is 2 or more, while the ingestion period (period from the first ingestion to the last ingestion) of the agent of the present invention is not particularly limited, it is generally 6 hr to 4 weeks. To exhibit improvement effect on exercise-induced gastrointestinal disorders, it is preferably 1 day to 2 weeks, more preferably 3 days to 1 week. In one embodiment, the agent of the present invention can be used to be taken 1 to 5 times (preferably 1 to 3 times) per day from one day to 2 weeks before (preferably 3 days to 1 week before) starting exercise. When ingested after completion of the exercise, the agent can be used to be ingested 1 to 3 times immediately after completion of exercise to after 24 hr (preferably immediately after to 6 hr).

In the present invention, cystine, or cystine and at least one selected from the group consisting of glutamine, serine, histidine, arginine, valine, leucine and isoleucine may be contained singly or in any combination in two or more preparations, or all may be contained in a single preparation. When these active ingredients are contained in two or more preparations, the timing of ingestion of each preparation may be simultaneous or separately, and also, the pathways of ingestion of respective preparations may be the same or different. An embodiment containing all active ingredients in one preparation is preferable for the agent of the present invention, since it can be ingested conveniently. When a medicament to be used in combination exists, the timing of ingestion thereof can be appropriately determined depending on the kind and effect.

In the present invention, when cystine, or cystine and at least one selected from the group consisting of glutamine, serine, histidine, arginine, valine, leucine and isoleucine is/are contained in two or more preparations, the content of these active ingredients (content per one intake by human, content relative to all amino acids contained in the agent of the present invention) and weight ratio are to be calculated by totaling the amount contained in each preparation.

The agent of the present invention can be used by adding to various foods. When the agent of the present invention is added to food, the food is not particularly limited, and may be any as long as it is a normal diet form. For example, the agent of the present invention can be added to drinks, and a suitable flavor is added when desired to give drink (e.g., beverage etc.). More specifically, the agent of the present invention can be added to, for example, juice, cow milk, confectionery, jelly, yogurt, candy and the like.

In addition, it is also possible to add the agent of the present invention to food, and provide same as food with health claims or dietary supplement. As used herein, the "food with health claims" includes food for specified health uses and food with nutrient function claims and the like. The "food for specified health uses" is, for example, a food that can indicate that a particular health object, for example, improvement of gastrointestinal disorder can be expected. In addition, the "food with nutrient function claims" is a food that can display the function of its nutritional components when the amount of nutritional components contained in the adequate intake per day meets the standards of the upper and lower limit specified by the national government. The "dietary supplement" includes so-called nutritional supplementary food or health supplementary food and the like. In the present invention, the "food for specified health uses" also includes a food with an indication that it is used for applications such as gastrointestinal disorder and the like, and further, a food containing a document stating that it is used for such applications (so-called statement of efficacy) and the like as a package and the like.

Furthermore, the agent of the present invention can be utilized by adding to a high density liquid diet or food supplement. When added to a food supplement, it can be prepared in a form such as tablet, capsule, powder, granule, suspension, chewable, syrup and the like by adding other components when desired. The "food supplement" in the present invention refers to one ingested to aid nutrition other than one ingested as a food, and also includes nutritional supplement, supplement and the like. The "high density liquid diet" is a comprehensive nutritional food (liquid food) designed based on the daily nutritional requirement and adjusted to a concentration of about 1 kcal/ml, for which the qualitative composition of each nutrient is sufficiently considered to ensure that no significant excess or deficiency of nutrients occurs even with single, long-term ingestion.

Since the agent of the present invention can be used by adding to various foods as mentioned above, a food composition for improving exercise-induced gastrointestinal disorder, containing cystine as an active ingredient is also provided according to the present invention. It is also possible to use the agent of the present invention itself as a food composition containing at least one or more food materials. The "food composition" in the present invention is a concept widely encompassing those orally ingestible, and also includes drinks, seasoning and the like.

The agent of the present invention can be formulated as a unit package form. In the present invention, the "unit package form" means a form of one or more units with a particular amount (e.g., one intake etc.) as one unit is/are packed in one package. For example, a unit package form with one intake as one unit is referred to as "unit package form per intake". A package used for the unit package form can be appropriately selected according to the form and the like of the agent of the present invention. For example, paper container, plastic container, aluminum can, steel can, glass bottle, plastic bottle, PTP sheet and the like can be mentioned.

The present invention also provides a commercial package comprising the agent of the present invention and a written matter stating that the agent of the present invention can or should be used for improving an exercise-induced gastrointestinal disorder (e.g., exercise-induced decline in gastrointestinal tract barrier function etc.).

The agent of the present invention can improve exercise-induced gastrointestinal disorder by ingestion (administration) of an effective amount thereof at least one time by a subject in need thereof. Particularly, the agent of the present invention can improve exercise-induced decline in gastrointestinal tract barrier function (preferably, decline in barrier function of small intestine and/or large intestine) and/or exercise-induced gastrointestinal upset by ingestion of an effective amount thereof at least one time by a subject in need thereof.

The present invention also provides a method of improving an exercise-induced gastrointestinal disorder (e.g., exercise-induced decline in gastrointestinal tract barrier function, and exercise-induced gastrointestinal upset etc.) by ingestion (administration) of an effective amount thereof at least one time by a subject in need thereof.

The method may exclude medical practice. Here, the "medical practice" refers to an act of treating, operating on or diagnosing a human, which is performed by a doctor or a dentist or under instruction and supervision of a doctor or a dentist.

Other features of the invention will become apparent in the course of the following descriptions of exemplary embodiments which are given for illustration of the invention and are not intended to be limiting thereof.

EXAMPLES

1. Improving Effect of Cystine on Exercise-Induced Decline in Gastrointestinal Tract Barrier Function It is known that high molecular weight substances that are not usually absorbed from the gastrointestinal tract penetrate the intestine and enter the blood when the barrier function of the gastrointestinal tract is declined (FIG. 1). Therefore, the improving effect of cystine on exercise-induced decline in gastrointestinal tract barrier function was studied by the following test.

Figure 2:
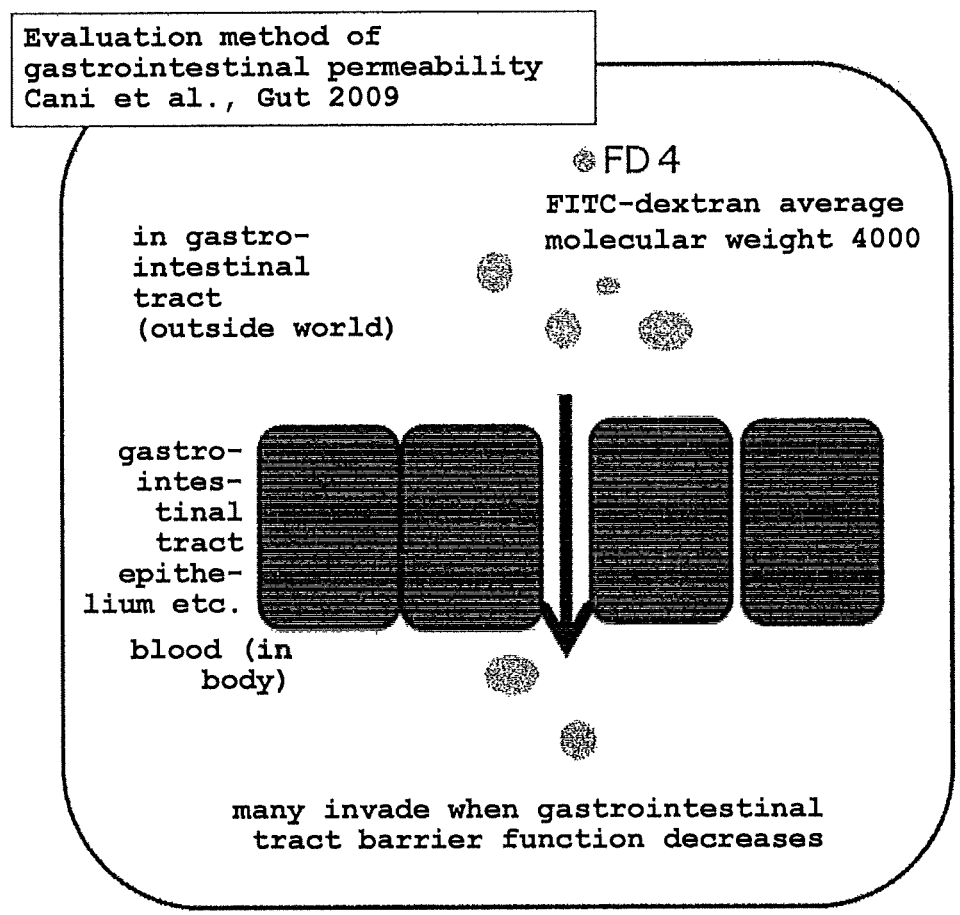
FIG. 2 is a schematic figure showing the evaluation method of Example 1.

7-Week-old male CD2F1 mice (Charles River Laboratories Japan, Inc.) were divided into 4 groups (Sed, Ex, Gln+Ex and Cyt+Ex), and a normal diet (AIN-93G composition) was given to Sed and Ex, a normal diet (AIN-93G composition) added with glutamine (2%) was given to Gln+Ex, and a normal diet (AIN-93G composition) added with cystine (2%) was given to Cyt+Ex, each for 7 days. Thereafter, each group was fasted overnight, and Ex, Gln+Ex and Cyt+Ex were made to run in a hamster wheel for 4 hr (speed: 10.5 m/min). While Ex, Gln+Ex and Cyt+Ex ran, fasting was continued for Sed. After completion of running, FITC-dextran (average molecular weight 4000; FD4, Sigma-Aldrich Japan) was orally administered to each group at a dose of 500 mg/kg body weight, and blood samples were collected after lapse of 1 hr. According to the method described in Cani et al., Gut 2009, 58(8): 1091-1103, which is incorporated herein by reference in its entirety, FD4 concentration that leaked into the blood from the gastrointestinal tract was calculated by measuring the fluorescence intensity in the blood, based on which the gastrointestinal tract permeability of FD4 was evaluated (see FIG. 2). To be specific, blood was collected from the mice under isoflurane anesthesia, the collected blood was centrifuged to give plasma, the obtained plasma was diluted 2-fold with phosphate buffer, and fluorescence intensity was measured under the conditions of excitation wavelength: 485 nm, detection wavelength: 535 nm (measurement device SPECTRA MAX GEMINI EM Molecular Devices Japan).

Figure 3:
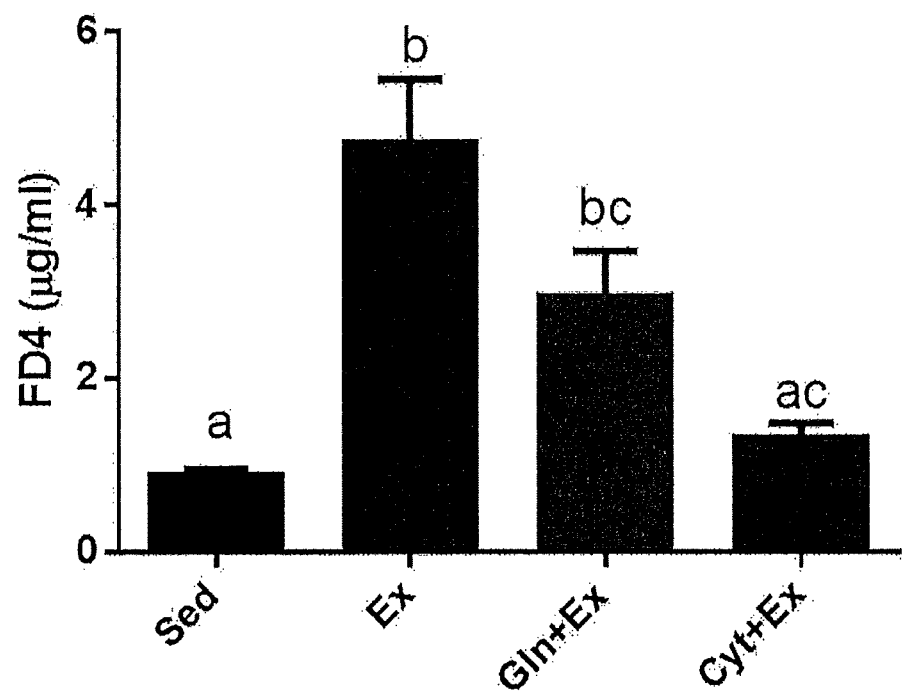
FIG. 3 is a graph showing an improving effect of cystine on exercise-induced decline in gastrointestinal tract barrier function. Sed: group with ingestion of normal diet and without exercise, Ex: group with ingestion of normal diet and exercise, Cyt+Ex: group with ingestion of normal diet added with cystine and with exercise, Gln+Ex: group with ingestion of normal diet added with glutamine and with exercise. Among different symbols a, b, c, P<0.05.

The results are shown in FIG. 3 (among different symbols a, b, c, P<0.05). The group (Ex) given a normal diet and made to do exercise showed a higher FD4 concentration in blood as compared to the group (Sed) given a normal diet and free of exercise. The results confirm that the 4 hr running decreased the gastrointestinal tract barrier function, and many high molecular weight substances flowed into the blood from the gastrointestinal tract. The group (Cyt+Ex) given a normal diet added with cystine and made to do exercise showed a lower FD4 concentration in blood as compared to Ex. It was found from the results that cystine improves exercise-induced decline in gastrointestinal tract barrier function. In addition, Cyt+Ex showed a lower FD4 concentration in blood as compared to the group (Gln+Ex) given a normal diet added with glutamine and made to do exercise. It was found from the results that cystine shows a higher improving effect than glutamine at the same dose on exercise-induced decline in gastrointestinal tract barrier function.

2. Improving Effect of Cystine on Exercise-Induced Decrease in Appetite

Athletes are known to experience gastrointestinal upset and loss of appetite in scenes where intense training such as a camp training and the like are repeated. Therefore, the improving effect of cystine on exercise-induced decrease in appetite was studied by the following test.

Figure 4:
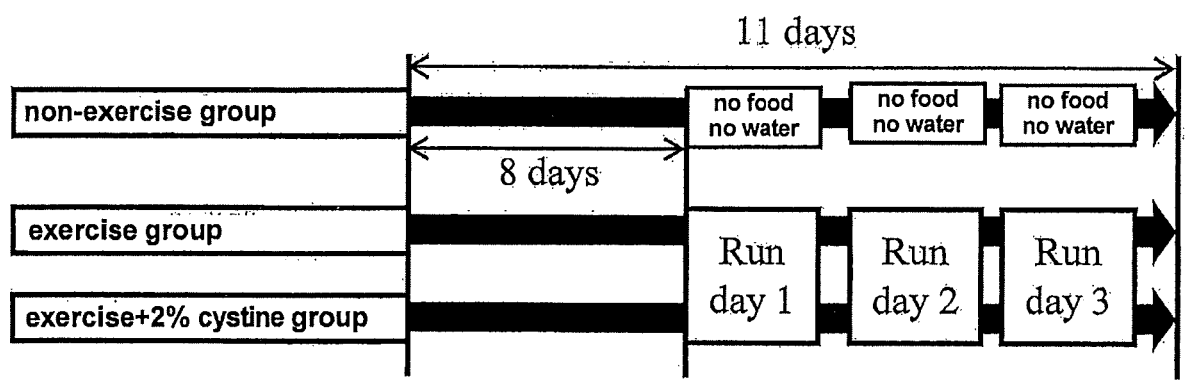
FIG. 4 is a figure showing the protocol of Example 2.

6-Week-old male CD2F1 mice (Charles River Laboratories Japan, Inc.) were divided into 3 groups (non-exercise group, exercise group, and exercise+2% cystine group), and a normal diet (AIN-93G composition) was given to non-exercise group and exercise group, and a normal diet (AIN-93G composition) added with cystine (2%) in place of casein was given to exercise+2% cystine group, each for 8 days. Thereafter, exercise group and exercise+2% cystine group were made to run in a treadmill to total exhaustion for 3 consecutive days, and non-exercise group was not allowed to exercise (see FIG. 4). While exercise group and exercise+2% cystine group ran, non-exercise group was fasted and deprived of water. A new feed was given every day after completion of the totally exhausting exercise, recovered the next day and the amount of the remaining feed was measured, from which feed intake was calculated.

Figure 5:
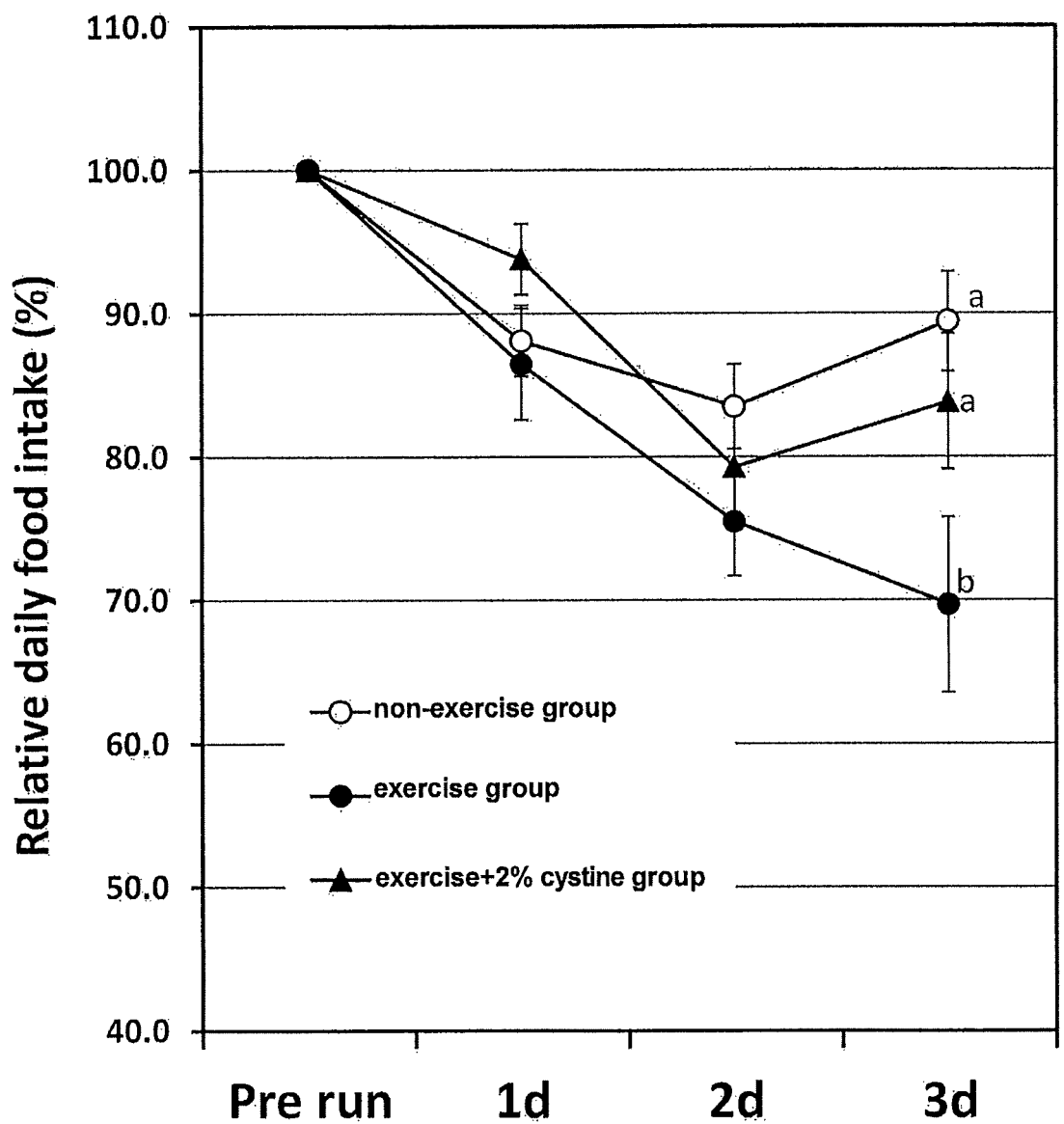
FIG. 5 is a graph showing an improving effect of cystine on exercise-induced decrease in appetite. Non-exercise group: group with ingestion of normal diet and without exercise, exercise group: group with ingestion of normal diet and with totally exhausting exercise for 3 consecutive days, exercise+2% cystine group: group with ingestion of normal diet added with cystine and with exercise. Between different symbols a, b, P<0.05.

FIG. 5 shows the results of relative feed intake when the feed intake of each group before continuous loading with totally exhausting exercise (Pre run) as 100% (between different symbols a, b, P<0.05). The group given a normal diet and made to do totally exhausting exercise for 3 consecutive days (exercise group) showed a significant decrease in the feed intake on day 3 of exercise loading as compared to the group given a normal diet and free of exercise (non-exercise group). The results suggest that gastrointestinal upset (appetite decrease) increased and feed intake decreased due to the totally exhausting exercise for 3 consecutive days. The group given a normal diet added with cystine and with exercise (exercise+2% cystine group) showed suppressed feed intake after exercise as compared to the exercise group, and the feed intake after totally exhausting exercise for 3 consecutive days was significantly high as compared to the exercise group. The results revealed that cystine improves exercise-induced gastrointestinal upset (appetite decrease).

3. Improving Effect of Combined Use of Cystine and Glutamine on Exercise-Induced Decline in Gastrointestinal Tract Barrier Function 7-Week-old male CD2F1 mice (Charles River Laboratories Japan, Inc.) were divided into 3 groups (Sed, Ex, GC+Ex), and a normal diet (AIN-93G composition) was given to Sed and Ex, and a normal diet (AIN-93G composition) added with an amino acid composition (3.2%) constituted of glutamine and cystine (weight ratio 30:7) was given to GC+Ex, each for 7 days. Thereafter, each group was fasted overnight, and Ex and GC+Ex were made to run in a hamster wheel for 4 hr (speed: 10.5 m/min). While Ex and GC+Ex ran, fasting was continued for Sed. After completion of running, the gastrointestinal tract permeability of FD4 was evaluated in the same manner as in Example 1.

Figure 6:
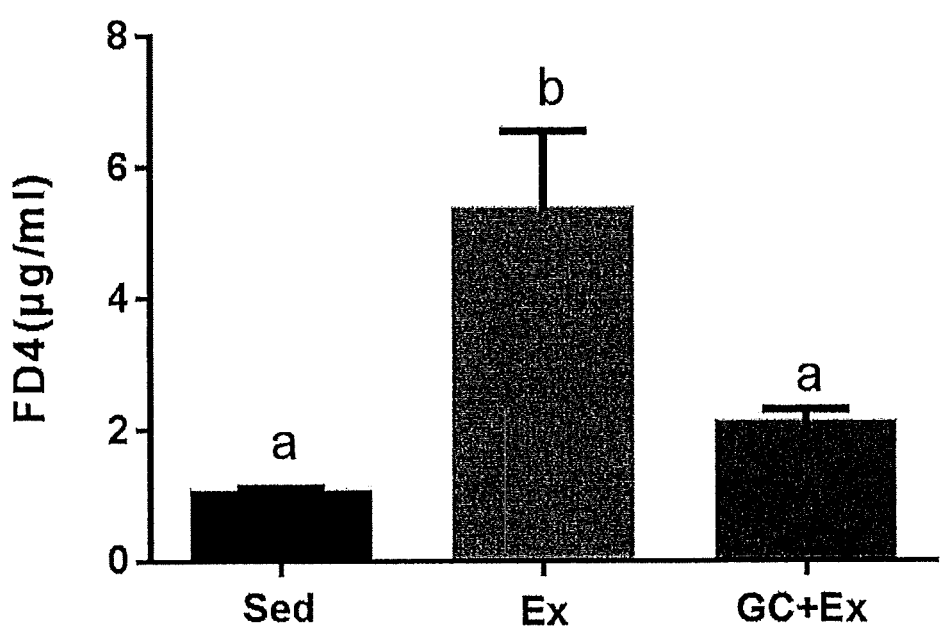
FIG. 6 is a graph showing an improving effect of combined use of cystine and glutamine on exercise-induced decline in gastrointestinal tract barrier function. Sed: group with ingestion of normal diet and without exercise, Ex: group with ingestion of normal diet and exercise, GC+Ex: group with ingestion of normal diet added with amino acid composition containing glutamine and cystine and with exercise. Between different symbols a, b, P<0.05.

The results are shown in FIG. 6 (between different symbols a, b, P<0.05). The group (Ex) given a normal diet and made to do exercise showed a higher FD4 concentration in blood as compared to the group (Sed) given a normal diet and free of exercise. The results confirm that the 4 hr running decreased the gastrointestinal tract barrier function, and many high molecular weight substances flowed into the blood from the gastrointestinal tract. The group (GC+Ex) given a normal diet added with an amino acid composition containing glutamine and cystine and made to do exercise showed a lower FD4 concentration in blood as compared to Ex. It was found from the results that an amino acid composition containing glutamine and cystine improves exercise-induced decline in gastrointestinal tract barrier function.

INDUSTRIAL APPLICABILITY

The agent of the present invention is preferably used for improving an exercise-induced gastrointestinal disorder. Particularly, the agent of the present invention is effectively used for improving exercise-induced decline in gastrointestinal tract barrier function (preferably, decline in barrier function of small intestine and/or large intestine) and/or exercise-induced gastrointestinal upset.

In addition, since the agent of the present invention contains amino acid with rich eating experiences such as cystine and the like as an active ingredient, it is extremely advantageous since it has high safety and scarce side effects.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of reducing a risk of a gastrointestinal disorder induced by an exercise, comprising:
administering an effective amount of an agent containing cystine or a salt thereof as an active ingredient at least one time to a subject who does not have a gastrointestinal disorder; and
subjecting the subject to an exercise after the administration.

2. The method according to claim 1, wherein said gastrointestinal disorder is at least one disorder selected from decline in gastrointestinal tract barrier function and gastrointestinal upset.

3. The method according to claim 1, wherein a content of cystine or a salt thereof is not less than 0.1 wt % relative to the weight of all amino acids contained in said agent.

4. The method according to claim 1, wherein said cystine or a salt thereof is in ingested in an amount of 6 mg to 12 g per one intake by a human.

5. The method according to claim 1, further comprising ingesting at least one member selected from the group consisting of glutamine, a salt of glutamine, serine, a salt of serine, histidine, a salt of histidine, arginine, a salt of arginine, valine, a salt of valine, leucine, a salt of leucine, isoleucine, and a salt of isoleucine.

6. The method according to claim 5, wherein a total of a content of said cystine or a salt thereof and a content of said at least one member selected from the group consisting of glutamine, a salt of glutamine, serine, a salt of serine, histidine, a salt of histidine, arginine, a salt of arginine, valine, a salt of valine, leucine, a salt of leucine, isoleucine, and a salt of isoleucine is not less than 10 wt % relative to the weight all amino acids contained in said agent.

7. The method according to claim 5, wherein in said agent a weight ratio of (a) a content of said cystine or a salt thereof, and (b) a content of at least one member selected from the group consisting of glutamine, a salt of glutamine, serine, a salt of serine, histidine, a salt of histidine, arginine, a salt of arginine, valine, a salt of valine, leucine, a salt of leucine, isoleucine, and a salt of isoleucine is (a):(b)=1:0.01 to 10.

8. The method according to claim 1, wherein said ingesting is oral ingestion.

9. The method according to claim 1, further comprising:
administering said agent during the exercise or after completion of the exercise.

10. The method according to claim 1, wherein said agent comprises cystine or a salt thereof in an amount of not less than 3 wt % relative to the weight of all amino acids contained in said agent.

11. The method according to claim 1, wherein said agent further comprises glutamine or a salt of glutamine.

12. The method according to claim 1, wherein said agent comprises cystine or a salt thereof in an amount of not less than 3 wt % relative to the weight of all amino acids contained in said agent, and said agent further comprises glutamine or a salt of glutamine.

* * * * *